United States Patent [19]

Jendralla et al.

[11] Patent Number: 5,519,113
[45] Date of Patent: May 21, 1996

[54] PROCESS FOR THE DIASTEREOSELECTIVE REDUCTIVE PINACOL COUPLING OF HOMOCHIRAL α-AMINOALDEHYDES

[75] Inventors: Joachim-Heiner Jendralla; Detlef Jacobi; Bernhard Kammermeier, all of Frankfurt, Germany

[73] Assignee: Hoechst Aktiengesellschaft, Frankfurt am Main, Germany

[21] Appl. No.: 259,135

[22] Filed: Jun. 13, 1994

Related U.S. Application Data

[63] Continuation of Ser. No. 852,614, Mar. 12, 1992, abandoned.

[30] Foreign Application Priority Data

Mar. 15, 1991 [DE] Germany ............................ 41 08 357.1
Jul. 11, 1991 [DE] Germany ............................ 41 22 911.8

[51] Int. Cl.$^6$ ..................................................... C07K 1/02
[52] U.S. Cl. ........................... 530/322; 530/338; 530/339
[58] Field of Search .................................... 530/333, 332, 530/331, 330, 329, 338, 339, 322

[56] References Cited

FOREIGN PATENT DOCUMENTS 0402646  12/1990  European Pat. Off. ....... C07D 213/40
WO91/18866  12/1991  WIPO .......................... C07C 237/22

OTHER PUBLICATIONS

Morrison and Boyd, Organic Chemistry, 4th Ed. Chapter 30, pp. 1117–1120 (1983).

A. W. Konradi et al., "Synthesis of 3–Amino–1,2–Diols Via the Cross Pinacol Coupling of N–Protected α–Amino Aldehydes and Aliphatic Aldehydes Using [V$_2$Cl$_3$(THF)$_6$]$_2$ [Zn$_2$Cl$_6$]," Abstracts of the 199th Meeting of the American Chemical Society, Apr. 22–27, 1990, ORGN 409.

D. J. Kempf et al., "Structure–Based, C$_2$ Symmetric Inhibitors of HIV Protease," *J. Med. Chem.*, 1990, 33, 2687–2689.

A. W. Konradi et al., "Pinacol Homocoupling of (S)–2– [N–(Benzyloxy–carbonyl)amino] Aldehydes by [V$_2$Cl$_3$(THF)$_6$]$_2$[Zn$_2$Cl$_6$]. Synthesis of C$_2$–Symmetric (1S, 2R,3R,4S)–1,4–Diamino 2,3–Diols," *J. Org. Chem.*, 1992.

A. W. Konradi et al., Journal of Organic Chemistry, vol. 55, pp. 4506–4508 (1990).

P. M. Takahara et al., Tetrahedron Letters, vol. 30, No. 51, pp. 7177– 7180 (1989).

J. H. Freudenberger et al., Journal of the American Chemical Society, vol. 111, pp. 8014–8016 (1989).

*Primary Examiner*—Jeffrey E. Russel
*Attorney, Agent, or Firm*—Finnegan, Henderson, Farabow, Garrett & Dunner

[57] ABSTRACT

Process for the diastereoselective reductive pinacol coupling of homochiral α-aminoaldehydes A process for the preparation of optically pure symmetrical compounds of the formula I

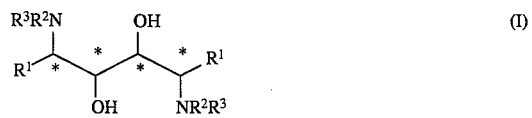

is described, in which $R^1$, $R^2$ and $R^3$, are explained in the description, with simultaneous control of the four centers of chirality indicated by *.

7 Claims, No Drawings

PROCESS FOR THE DIASTEREOSELECTIVE REDUCTIVE PINACOL COUPLING OF HOMOCHIRAL α-AMINOALDEHYDES

This application is a continuation of application Ser. No. 07/852,614 filed Mar. 12, 1992, now abandoned.

The invention relates to a process for the preparation of optically pure symmetrical compounds of the formula I

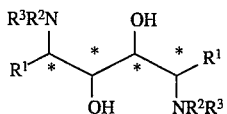  (I)

in which $R^1$, $R^2$ and $R^3$ are described in greater detail below, with simultaneous control of the four choral centers indicated by *.

In EP-A-0,402,646 and D. J. Kempf et al. [J. Med. Chem. 33, 2687 (1990)], the preparation is described of compounds of the above type using McMurry reagent [$TiCl_3$/Zn(Cu)]. This reductive coupling method leads to mixtures which are difficult to separate. As reported in the above-cited works, the three diastereomers are produced in about the same amount and in poor yield.

S. F. Pedersen et al. [J. Am. Chem. Soc.111,8014 (1989)] report that, by means of the vanadium(II) complex [$V_2Cl_3(THF)_6]_2[Zn_2Cl_6$] in the reductive cross-coupling of achiral linear aliphatic aldehydes with 3-formyl-propanamides, syn-diols may be obtained diastereoselectively, constitutionally unsymmetrical compounds resulting from the use of different carbonyl compounds.

It is an aim of the present invention to find a simpler and stereoselective process, free from the known disadvantages, for the preparation of the abovementioned compounds.

The invention is realized by the process for the preparation of compounds of the formula I

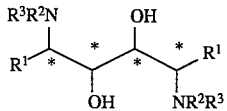  (I)

in which
$R^1$ is a side chain radical of a natural or synthetic α-amino acid;
$R^2$ and $R^3$ are identical or different and
a) are each hydrogen
b) are each a radical of the formula D-(E)$_n$-(F)$_o$-(G)$_p$  (II)

where E, F and G independently of each other are a natural or synthetic amino acid, azaamino acid or imino acid;
n, o, and p independently of each other are 0 or 1;
D is $R^4$ or a radical of the formula III, IV or V

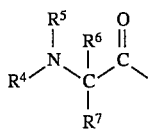  (III)

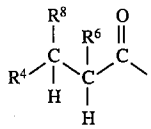  (IV)

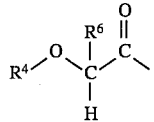  (V)

in which $R^4$ is
b$_1$) hydrogen,
carboxyl,
($C_1$–$C_{18}$)-alkyl, which is optionally monounsaturated or diunsaturated and which is unsubstituted or substituted by up to 3 identical or different radicals selected from the group comprising
mercapto,
hydroxyl,
($C_1$–$C_7$)-alkoxy,
carbamoyl,
($C_1$–$C_8$)-alkanoyloxy
carboxyl,
($C_1$–$C_7$)-alkoxycarbonyl,
F, Cl, Br, I,
amino,
amidino, which can be unsubstituted or substituted by one, two or three ($C_1$–$C_8$)-alkyl radicals,
guanidino, which can be unsubstituted or substituted by one or two benzyloxycarbonyl radicals or by one, two, three or four ($C_1$–$C_8$)-alkyl radicals,
($C_1$–$C_7$)-alkylamino,
di-($C_1$–$C_7$)-alkylamino,
($C_1$–$C_6$)-alkoxycarbonylamino,
($C_1$–$C_{15}$)-aralkoxycarbonyl,
($C_7$–$C_{15}$)-aralkoxycarbonylamino,
phenyl-($C_1$–$C_4$)-alkoxy,
9-fluorenylmethoxycarbonylamino,
($C_1$–$C_6$)-alkylsulfonyl,
($C_1$–$C_6$)-alkylsulfinyl,
($C_1$–$C_6$)-alkylthio,
hydroxamino,
hydroximino,
sulfamoyl,
sulfo,
carboxamido,
formyl,
hydrazono,
imino,
and a $CONR^9R^{10}$ radical, or
by up to six hydroxyl groups or
by up to five ($C_1$–$C_8$)-alkanoyloxy groups;
mono-, bi- or tricyclic ($C_3$–$C_{18}$)-cycloalkyl, ($C_3$–$C_{18}$)-cycloalkyl-($C_1$–$C_5$)-alkyl, the cycloalkyl moiety in each case being unsubstituted or substituted by one or two identical or different radicals selected from the group comprising
F, Cl, Br, I,
carboxyl,
carbamoyl,
carboxymethoxy,
hydroxyl,
($C_1$–$C_7$)-alkoxy,
($C_1$–$C_7$)-alkyl ($C_1$–$C_7$)-alkyloxycarbonyl,
amino,
($C_1$–$C_6$)-alkylamino-($C_1$–$C_6$)-alkyl,
di-($C_1$–$C_6$)-alkylamino-($C_1$–$C_6$)-alkyl,
amidino,
hydroxamino,
hydroximino,
hydrazono,
imino,
guanidino,
($C_1$–$C_6$)-alkoxysulfonyl,
($C_1$–$C_6$)-alkoxysulfinyl,
($C_1$–$C_6$)-alkoxycarbonylamino,
($C_6$–$C_{12}$)-aryl-($C_1$–$C_4$)-alkoxycarbonylamino,
($C_1$–$C_7$)-alkylamino,
di- ($C_1$–$C_7$)-alkylamino and
trifluoromethyl;
($C_6$–$C_{14}$)-aryl,
($C_6$–$C_{14}$)-aryl-($C_1$–$C_6$)-alkyl,
($C_6$–$C_{14}$)-aryloxy-($C_1$–$C_6$)-alkyl or
($C_6$–$C_{14}$)-aryl-($C_3$–$C_6$)-cycloalkyl,
in which the aryl moiety in each case is unsubstituted or substituted by one, two or three identical or different radicals selected from the group comprising
F, Cl, Br, I,
hydroxyl,
mono-, di- or trihydroxy-($C_1$–$C_4$)-alkyl,
trifluoromethyl,
formyl,
carboxamido,
mono- or di-($C_1$–$C_4$)-alkylaminocarbonyl,
nitro,
($C_1$–$C_7$)-alkoxy,
($C_1$–$C_7$)-alkyl,
($C_1$–$C_7$)-alkoxycarbonyl,
amino,
($C_1$–$C_7$)-alkylamino,
di-($C_1$–$C_7$)-alkylamino,
carboxyl,
carboxymethoxy,
amino-($C_1$–$C_7$)-alkyl,
($C_1$–$C_7$)-alkylamino-($C_1$–$C_7$)-alkyl,
di-($C_1$–$C_7$)-alkylamino-($C_1$–$C_7$)-alkyl,
($C_1$–$C_7$)-alkoxycarbonylmethoxy,
carbamoyl,
sulfamoyl,
($C_1$–$C_7$)-alkoxysulfonyl,
($C_1$–$C_8$)-alkylsulfonyl,
sulfo-($C_1$–$C_8$)-alkyl,
guanidino-($C_1$–$C_8$)-alkyl and
($C_1$–$C_6$)-alkoxycarbonylamino;
het,
het-($C_1$–$C_6$)-alkyl,
het-($C_3$–$C_8$)-cycloalkyl,
het-($C_3$–$C_6$)-cycloalkyl-($C_1$–$C_4$)-alkyl,
het-($C_3$–$C_8$)-cycloalkoxy-($C_1$–$C_4$)-alkyl,
het-thio-($C_1$–$C_6$)-alkyl,
het-thio-($C_3$–$C_8$)-cycloalkyl,
het-thio-($C_3$–$C_8$)-cycloalkyl-($C_1$–$C_4$)-alkyl,
where het is in each case the radical of a 5- to 7-membered monocyclic or 8- to 10-membered bicyclic ring system, which may be fused to a benzene ring, be aromatic, or partially or completely hydrogenated, which can contain as hetero elements one, two, three or four different radicals selected from the group comprising N, O, S, NO, SO, and $SO_2$, which can be substituted by 1 to 6 hydroxyl groups and which is optionally defined as for ($C_6$–$C_{14}$)-aryl under $b_1$) and/or is mono-, di- or trisubstituted by oxo, or is an $NR^9R^{10}$ radical, or $b_2$) a radical of the formula VI $$R^{4a}\text{-W} \qquad (VI)$$

in which $R^{4a}$ is defined as for $R^4$ under $b_1$) and W is —CO—, —CS—, O—CO—, —$SO_2$—, —SO—, —S—, —$NHSO_2$—, —NHCO—, —CH(OH)—, —N(OH)— or —CO—V—, V being a peptide having a total of 1 to 10 amino acids, imino acids and/or azaamino acids; or in which $R^4$ together with $R^8$ and the atoms bearing these form mono- or bicyclic, saturated or partially unsaturated ring systems having 5–12 ring members, which can also contain, apart from carbon, 1 sulfur atom which can optionally be oxidized to the sulfoxide or sulfone;

$b_3$) a glycosyl radical, preferably a glucofuranosyl or glucopyranosyl radical, which is derived from naturally occurring aldotetroses, aldopentoses, aldohexoses, ketopentoses, ketohexoses, deoxyaldoses, aminoaldoses and oligosaccharides and their stereoisomers; or $b_4$) an amino-protecting group;

$R^5$ is hydrogen or
($C_1$–$C_8$)-alkyl, or
together with $R^6$ and the atoms bearing this radical forms mono- or bicyclic, saturated or partially unsaturated ring systems having 5–12 ring members;
$R^6$ is defined as for $R^4$ under $b_1$);
is hydroxyl or ($C_1$–$C_4$)-alkanoyloxy; or
together with $R^7$ and the atoms bearing this radical forms cyclic, saturated or partially unsaturated ring systems having 3 to 12 ring members; or
together with $R^8$ and the atoms bearing this forms a mono- or bicyclic, saturated or partially unsaturated ring system having 5–12 ring members, which can also contain, apart from carbon, 1 sulfur atom which can optionally be oxidized to the sulfoxide or sulfone; or can contain 1 nitrogen atom, where the ring system can be unsubstituted or substituted by amino;
$R^7$ is hydrogen or
($C_1$–$C_6$)-alkyl;
$R^8$ is hydrogen,
hydroxyl,
($C_1$–$C_4$)-alkanoyloxy or
($C_1$–$C_8$)-alkyl;
$R^9$ and $R^{10}$ are each
hydrogen,
($C_1$–$C_8$)-alkyl, which can be substituted by amino,
($C_1$–$C_4$)-alkylamino,
di-($C_1$–$C_4$)-alkylamino,
mercapto,
carboxyl,
hydroxyl or
($C_1$–$C_4$)-alkoxy, ($C_3$–$C_7$)-cycloalkyl, ($C_1$–$C_4$)-alkoxycarbonyl, ($C_6$–$C_{14}$)-aryl, ($C_6$–$C_{14}$)-aryl-($C_1$–$C_4$)-alkoxycarbonyl, which can be substituted in the aryl moiety as described for $R^4$, het or het-($C_1$–$C_4$)-alkyl, het being defined as described for $R^4$, or $R^9$ and $R^{10}$ together with the nitrogen atom bearing them forming monocyclic or bicyclic, saturated, partially unsaturated or aromatic ring systems which contain as ring members, in addition to carbon, 1 or 2 further nitrogen atoms, 1 sulfur atom or 1 oxygen atom and can be substituted by ($C_1$–$C_4$)-alkyl, where in the preceding compounds of the formula I one or more amide groups (—CONH—) of the main chain can be replaced by —$CH_2NR^{11}$—, —$CH_2S$—, —$CH_2O$—, —$OCH_2$—, —$CH_2CH_2$—, —CH=CH— (cis and trans), —$COCH_2$—, —CH(OH)$CH_2$—, —$CH_2SO$—, —$CH_2SO_2$—, —COO—, —P(O)(OR$^{12}$)$CH_2$— and —P(O)(OR$^{12}$)NH—, or alternatively by an amide group having reversed polarity (—NHCO—); in which $R^{11}$ and $R^{12}$ independently of each other are hydrogen or ($C_1$–$C_4$)-alkyl;

and their enantiomers and physiologically tolerated salts, which comprises treating homochiral α-aminoaldehydes of the formula VII

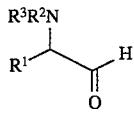

(VII)

in which $R^1$, $R^2$ and $R^3$ are defined as above, with [$V_2Cl_3$(THF)$_6$]$_2$[$Zn_2Cl_6$] or with a vanadium complex obtainable in situ from $VCl_3$, THF and zinc dust, a simultaneous control over all four chiral centers being present.

Preference is given to the preparation of compounds of the formula I, in which $R^1$ is a side chain radical of the α-amino acids Gly, Ala, Val, Leu, Ile, Ser, Thr, Cys, Met, Pro, Lys, Arg, His, Asp, Asn, Glu, Gln, Phe, Tyr, Trp or Cha;

$R^2$ and $R^3$ are identical or different, and are each a) hydrogen b) a radical of the formula II in which o and p=0, n=0 or 1 and E is one of the abovementioned α-amino acids, D is $R^4$ or a radical of the formula III or IV, in which $R^4$ is $b_1$) hydrogen ($C_1$–$C_9$)-alkyl, which is optionally monounsaturated or diunsaturated and which is unsubstituted or substituted by up to 3 identical or different radicals selected from the group comprising hydroxyl, ($C_1$–$C_7$)-alkoxy, carbamoyl, ($C_1$–$C_8$)-alkanoyloxy, ($C_1$–$C_7$)-alkoxycarbonyl, F, Cl, amino, ($C_1$–$C_7$)-alkylamino, di-($C_1$–$C_7$)-alkylamino, ($C_1$–$C_6$)-alkoxycarbonylamino, ($C_7$–$C_{15}$)-aralkoxycarbonyl, ($C_7$–$C_{15}$)-aralkoxycarbonylamino, phenyl-($C_1$–$C_4$)-alkoxy, 9-fluorenylmethoxycarbonylamino, ($C_1$–$C_6$)-alkylsulfonyl, ($C_1$–$C_6$)-alkylsulfinyl, and ($C_1$–$C_6$)-alkyl thio, ($C_6$–$C_{14}$)-aryl, ($C_6$–$C_{14}$)-aryl-($C_1$–$C_6$)-alkyl or ($C_6$–$C_{14}$)-aryloxy-($C_1$–$C_6$)-alkyl, in which the aryl moiety may in each case be unsubstituted or substituted by one, two or three identical or different radicals selected from the group comprising the abovementioned preferred substituents of ($C_1$–$C_9$)-alkyl, $b_2$) a radical of the formula VI, in which $R^{4a}$ is defined as for $R^4$ under $b_1$) and W is —CO—, O—CO—, —$SO_2$—, —SO—, —S—, —NHCO—, —CH(OH)—;

$b_4$) an amino-protecting group Fmoc, Z or Boc, $R^5$ and $R^7$ are each hydrogen, $R^6$ is defined as for $R^4$, and $R^8$ is hydrogen, hydroxyl, ($C_1$–$C_4$)-alkanoyloxy or ($C_1$–$C_8$)-alkyl.

Preference is further given to compounds of the formula I, in which one of the radicals $R^2$ and $R^3$ is hydrogen.

Furthermore, preference is given to compounds of the formula I having the SRRS-configuration (when aldehydes of the formula VII having the (S)-configuration are used) or to compounds of the formula I having the RSSR-configuration (when aldehydes of the formula VII having the (R)-configuration are used).

Very particular preference is given to compounds of the formula I, in which $R^1$ is a side chain radical of the α-amino acids Ala, Val, Leu, Ile, Pro, Phe, Cha or Tyr, $R^2$ and $R^3$ are identical or different and are each a) hydrogen b) a radical of the formula II, in which o and p=0, n is 0 or 1 and E is Ala, Val, Leu, Ile, Pro, Phe, Cha or Tyr;

D is $R^4$ or a radical of the formula IV where $R^4$ is $b_1$) hydrogen, ($C_1$–$C_4$)-alkyl, phenyl or naphthyl, phenylmethyl or naphthylmethyl, $b_2$) a radical of the formula VI, in which $R^{4a}$ is defined as for $R^4$ under $b_1$) and W is —CO—, —O—CO—, —$SO_2$—, —SO—, —S—, —NHCO—, —CH(OH)—, or $b_4$) an amino-protecting group Fmoc, Z or Boc, $R^5$, $R^7$ and $R^8$ are each hydrogen, and $R^6$ is defined as for $R^4$ under $b_1$).

Very particular preference is further given to compounds of the formula I having the SRRS-configuration, obtained by the use of aldehydes of the formula VII having (S) absolute configuration. This statement is only applicable on the condition that the $R^1$ group has a lower Cahn-Ingold-Prelog priority than the —CH(OH)—CH(OH)— group.

α-Amino acids, if they are chiral, can be present in the S- or R-form. They correspond to the formula VIII below

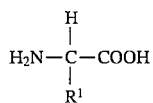
(VIII)

and differ only in the $R^1$ radical of the side chain. Some natural and synthetic α-amino acids are mentioned below as examples in the three letter code:

Aad, Abu, ABz, 2ABz, Ach, Acp, Adpd, Ahb, Aib, Ala, Alg, All, Ama, Amt, Ape, Apm, Apr, Arg, Asn, Asp, Asu, Aze, Azi, Bai, Bph, Can, Cha, Cit, Cys, $(Cys)_2$, Cyta, Daad, Dab, Dadd, Dap, Dapm, Dasu, DJen, Dpa, Dtc, Fel, Gln, Glu, Gly, Guv, hAla, hArg, hCys, hGln, hGlu, His, hIle, hLeu, hLys, hMet, hPhe, hPro, hSer, hThr, hTrp, Hyl, Hyp, 3Hyp, Ile, Ise, Iva, Kyn, Lant, Lcn, Leu, Lsg, Lys, Met, Mim, Min, nArg, Nle, Nva, Oly, Orn, Pan, Pec, Pen, Phe, Phg, Pic, Pro, Pse, Pya, Pyr, Pza, Qin, Ros, Sar, Sec, Sem, Ser, Thi, Thr, Thy, Thx, Tia, Tle, Tly, Trp, Trta, Tyr, Val, Nal, Tbg, Npg, Chg, Thia, Cha (see for example Houben-Weyl, "Methoden der organischen Chemie" [Methods in Organic Chemistry] vol. XV/1 and 2, Stuttgart 1974). Where not otherwise stated for individual compounds, the abbreviation of an amino acid radical without a sterochemical descriptor is the radical in the L-form, which normally corresponds to the S-configuration.

Imino acid is generally taken to mean natural or unnatural amino acids, whose amino group is monosubstituted. In this context, compounds may be particularly mentioned which are substituted by $(C_1-C_8)$-alkyl. In addition, heterocycles selected from the following group are of interest:

pyrrolidine-2-carboxylic acid; piperidine-2-carboxylic acid; 1,2,3,4-tetrahydro-isoquinoline-3-carboxylic acid; decahydroisoquinoline-3-carboxylic acid; octahydroindol-2-carboxylic acid; decahydroquinoline-2-carboxylic acid; octahydrocyclopenta[b]pyrrole-2-carboxylic acid; 2-azabicyclo[2.2.2]octane-3-carboxylic acid; 2-azabicyclo[2.2.1]heptane-3-carboxylic acid; 2-azabicyclo[3.1.0]hexane-3-carboxylic acid; 2-azaspiro[4.4]nonane-3-carboxylic acid; 2-azaspiro[4.5]decane-3-carboxylic acid; spiro[(bicyclo[2.2.1]heptane)-2,3-pyrrolidine-5-carboxylic acid];spiro[(bicyclo[2.2.2]octane)-2,3-pyrrolidine-5-carboxylic acid]; 2-azatri-cyclo[4.3.0.1$^{6,0}$]decane-3-carboxylic acid; decahydrocyclohepta[b]pyrrole-2-carboxylic acid; decahydrocycloocta[b]pyrrole-2-carboxylic acid; octahydrocyclopenta[c]pyrrole-2-carboxylic acid; octahydroisoindole-1-carboxylic acid; 2,3,3a,4,6a-hexahydrocyclopenta[b]pyrrole-2-carboxylic acid; 2,3,3a,4,5,7a-hexahydroindole-2-carboxylic acid; tetrahydrothiazole-4-carboxylic acid; isoxazolidine-3-carboxylic acid; pyrazolidine-3-carboxylic acid; hydroxyproline-2-carboxylic acid, all of which may be substituted or unsubstituted:

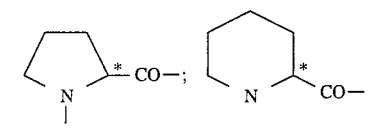

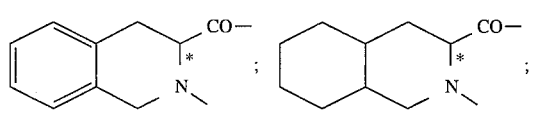

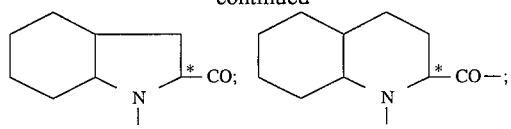

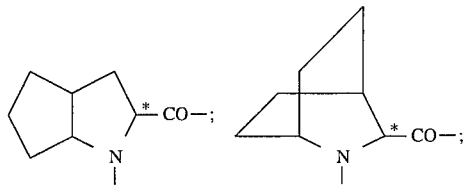

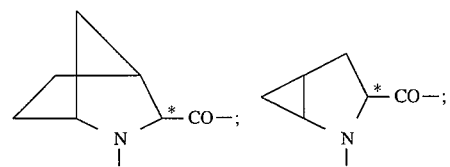

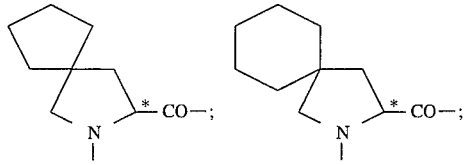

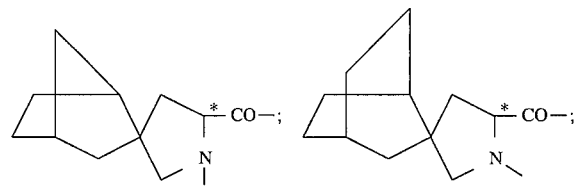

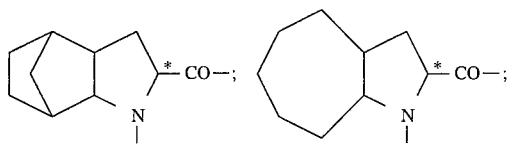

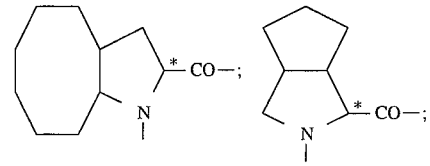

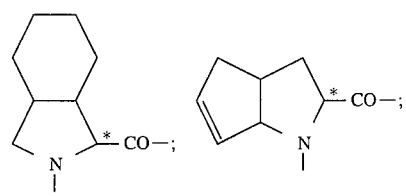

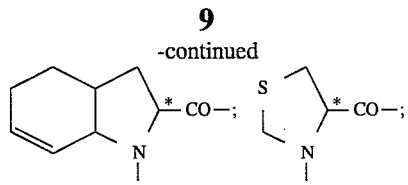
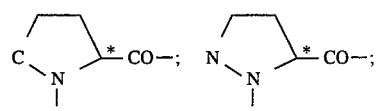
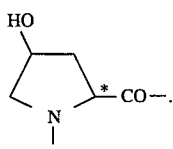

Azaamino acids are derived from natural or synthetic amino acids, the central —CHR— or —CH$_2$— unit being replaced by —NR— or —NH—, respectively.

A survey of the syntheses, in particular of the synthetic optically active α-amino acids and imino acids is given by R. M. Williams in "Synthesis of Optically Active α-Aminoacids", Pergamon Press, Oxford 1989.

The nomenclature used in this description follows the general practice for amino acids, that is the amino group is on the left and the carboxyl group on the right of each amino acid. This applies correspondingly to imino acids and azaamino acids.

Amino-protecting groups are described in R. Geiger and W. König "The Peptides" Volume 3 "Protection of Functional Groups in Peptide Synthesis", E. G. Gross, J. Meienhofer Edit., Academic Press, N.Y. (1981), in particular pages 7–46. Some are cited below as examples:

| | |
|---|---|
| H—CO— | For |
| CF$_3$—CO— | Pfa |
|  | Pht |
| CH$_3$—CO—CH$_2$—CO— | Aca |
| 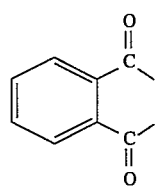 | Maleoyl |
| ClCH$_2$—CO— | Cla |
| 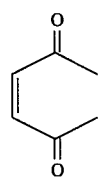 | 2-Nitrobenzoyl |

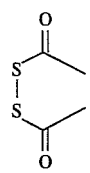

| | |
|---|---|
| Cysteic acid | Cys(O$_3$H) |

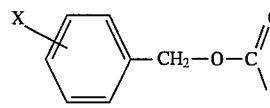

| | |
|---|---|
| X = H | Z |
| 2-Cl | 2Cz |
| 4-Cl | 4Cz |
| 4-Br | 4Bz |
| 3-Cl | 3Cz |
| 4-NO$_2$ | 4Nz |
| 4-(C$_6$H$_5$—N=N)— | Paz |
| 4-(CH$_3$O—C$_6$H$_5$—N=N)— | Mpaz |
| 4-CH$_3$ | Mez |
| 4-CH$_3$O | Moz |
| 4-CH$_3$CO—O | 4Acz |
| 4-(HO)$_2$B | Dobz |
| 2-CON(CH$_3$)$_2$ | 2-Dimethylamino-carbonyl-Z |
| 2,4-di-Cl | 2,4-Dcz |
| 3,4-di-Cl | 3,4-Dcz |
| 3,5-di-OCH$_3$ | 3,5-Dmoz |
| 2-NO$_2$-4,5-di-OCH$_3$ | 2N-3,5-Dmoz |

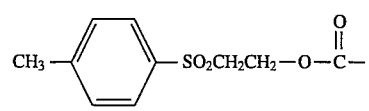

Tsc

CH$_3$—SO$_2$—CH$_2$—CH$_2$—O—CO—  Msc

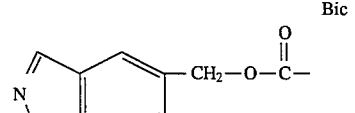

Bic

Ph$_3$P—CH$_2$—CH$_2$—O—CO—  Pec

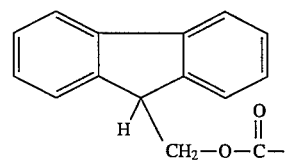

Fmoc

CH$_3$S—CH$_2$—CH$_2$—O—CO—  Mtc

| | |
|---|---|
| furfuryl-CH₂—O—CO— | Foc |
| pyridyl-CH₂—O—CO— | Inc |
| Br—CH₂—CH₂—O—CO— | Bec |
| I—CH₂—CH₂—O—CO— | Iec |
| Cl₃C—CH₂—O—CO— | Tcc |
| H₂C=CH—O—CO— | Voc |
| (iPr₂)₂—CH—O—CO— | Dmc |
| cyclopentyl-O—CO— | Cpc |
| 2-methylcyclohexyl-O—CO— | — |
| isobornyl-O—CO— | Ibc |
| Cholesteryl-O—CO— | Coc |
| Ph₂CH—O—CO— | Doc |
| (pyridyl)₂CH—O—CO— | Dpc |
| (CH₃)₃O—CO— | Boc |
| CH₃—CH₂—C(CH₃)₂—O—CO— | Aoc |
| adamantyl-O—CO— | Adc |
| 1-methylcyclobutyl-O—CO— | McBoc |
| 1-methylcyclohexyl-O—CO— | Mch |
| Ph—C(CH₃)₂—O—CO— | Poc |
| Ph—C₆H₄—C(CH₃)₂—O—CO— | Bpoc |
| 3,5-dimethoxyphenyl-C(CH₃)₂—O—CO— | Ddz |
| 4-methylphenyl-C(CH₃)₂—O—CO— | Mpc |
| pyridyl-C(CH₃)₂—O—CO— | — |
| N-methylpiperidinyl-C(CH₃)—O—CO— | — |
| (CH₃)₂N—CH₂—CH₂—CPh₂—O—CO— | — |
| (CH₃)₂N—CO—CH₂—CH₂—C(CH₃)₂—O—CO— | — |
| Ph—N=N—C₆H₄—C(CH₃)₂—O—CO— | Azc |
| NC—CH₂—C(CH₃)₂—O—CO— | Cyc |
| piperidinyl-N—O—CO— | — |
| (CH₃)₂N—O—CO— | — |
| CH₃—C₆H₄—SO₂—NH—CO— | Tac |
| 2-nitrophenyl-S— | Nps |
| CH₃—C₆H₄—SO₂— | Tosyl |
| (X—C₆H₄—CH₂—O)₂—PO— | Dbp |
| Ph₂P(O)— | Dpp |
| Ph₂P(S)— | Ppt |
| Ph₃C— | Trityl |
| Ph—CH= | — |
| R—CO—CH=C(CH₃)— | |
| R = CH₃ | Amv |
| C₆H₅ | Bmv |
| OC₂H₅ | — |
| NH₂ | — |
| dimedone-type | Dim |

Functional groups in the side chains of the amino acids, imino acids or azaamino acids can, for example, be protected as follows:

a) the guanidino group (for example of arginine) can be protected according to Geiger/König in E. Gross, J. Meinhofer ("The Peptides—Protection of Functional Groups in Peptide Synthesis", Academic Press, N.Y., 1981), pp. 60–70;

b) the amino nitrogen (for example of lysine) can be protected according to pp. 7–49;

c) the imidazole nitrogen (for example of histidine) can be protected according to pp. 70–80;

d) the pyrazolyl nitrogen (for example of β-3-pyrazolylalanine) can be protected according to pp. 81–82;

e) the indole nitrogen (for example of tryptophan) can be protected according to pp. 82–84;

f) the carboxyl group (for example of aspartic acid) can be protected according to pp. 102–132;

g) the sulfhydryl group (for example of cysteine) can be protected according to pp. 137–169;

h) the hydroxyl group (for example of serine, threonine, tyrosine) can be protected according to pp. 170–201;

i) for the case where $R^2$ corresponds to a peptide group, peptidic amide nitrogens can, if required, be protected according to pp. 52–59.

Glycosyl radicals such as those described above are derived in particular from natural substances occurring in microorganisms, plants, animals or humans, selected from the group comprising D- or L-monosaccharides such as ribose (Rib), arabinose (Ara), xylose (Xyl), lyxose (Lyx), allose (All), altrose (Alt), glucose (Glc), mannose (Man), gulose (Gul), idose (Ido), galactose (Gal), talose (Tal), erythrose (Ery), threose (Thr), psicose (Psi), fructose (Fru), sorbose (Sor), tagatose (Tag), xylulose (Xyu), fucose (Fuc), rhamnose (Rha), olivose (Oli), oliose (Olo), mycarose (Myc), rhodosamine (RN), N-acetylglucosamine (GlcNAc), N-acetylgalactosamine (GalNAc), N-acetylmannosamine (ManNAc) or disaccharides, such as maltose (Mal), lactose (Lac); cellobiose (Cel), gentibiose (Gen), N-acetyllactosamine (LacNAc), chitobiose (Chit), β-galactopyranosyl-(1–3)-N-acetyl-galactosamine and β-galactopyranosyl-(1–3)- or (1–4)-N-acetylglucosamine, and their synthetic derivatives, such as 2-deoxy-, 2-amino-, 2-acetamido- or 2-halo-, preferably bromo- and iodo-sugars.

Alkyl can be straight-chain or branched. This applies correspondingly to radicals derived therefrom, such as for example alkoxy, alkylthio, alkylamino, dialkylamino, alkanoyl and aralkyl.

Cycloalkyl is also taken to mean alkyl-substituted radicals, such as for example 4-methylcyclohexyl or 2,3-dimethylcyclopentyl.

$(C_6-C_{14})$-Aryl is for example phenyl, naphthyl, biphenylyl or fluorenyl; phenyl and naphthyl are preferred. This applies correspondingly to radicals derived therefrom, such as for example aryloxy, aroyl, aralkyl and aralkoxy. Aralkyl is taken to mean an unsubstituted or substituted $(C_6-C_{14})$-aryl radical coupled to a $(C_1-C_6)$-alkyl, such as for example benzyl, 1- and 2-naphthylmethyl, but aralkyl should not be restricted to the radicals mentioned.

Het radicals in the context of the preceding definition are pyrrolyl, furyl, thienyl, imidazolyl, pyrazolyl, oxazolyl, isoxazolyl, thiazolyl, isothiazolyl, tetrazolyl, pyridyl, pyrazinyl, pyrimidinyl, indolyl, isoindolyl, indazolyl, phthalazinyl, quinolyl, isoquinolyl, quinoxalinyl, quinazolinyl, cinnolinyl, β-carbolinyl, or a derivative of these radicals fused to a benzene ring, or fused to a cyclopentane, cyclohexane or cycloheptane ring.

These heterocycles can be substituted on a nitrogen atom by oxido; $(C_1-C_7)$-alkyl, for example methyl or ethyl; phenyl; phenyl-$(C_1-C_4)$-alkyl, for example benzyl; and/or on one or more carbon atoms by $(C_1-C_4)$-alkyl, for example methyl; phenyl; phenyl-$(C_1-C_4)$-alkyl, for example benzyl; halogen; hydroxy; $(C_1-C_4)$-alkoxy, for example methoxy; phenyl-$(C_1-C_4)$-alkoxy, for example benzyloxy; or oxo, and can be partially or completely saturated.

Radicals of this type are for example 2- or 3-pyrrolyl; phenylpyrrolyl, for example 4- or 5-phenyl-2-pyrrolyl; 2-furyl; 2-thienyl; 4-imidazolyl; methylimidazolyl, for example 1-methyl-2-, -4- or -5-imidazolyl; 1,3-thiazol-2-yl; 2-, 3- or 4-pyridyl; 2-, 3- or 4-pyridyl-N-oxide; 2-pyrazinyl; 2-, 4- or 5-pyrimidinyl; 2-, 3- or 5-indolyl; substituted 2-indolyl, for example 1-methyl-, 5-methyl-, 5-methoxy-, 5-benzyloxy-, 5-chloro- or 4,5-dimethyl-2-indolyl; 1-benzyl-2- or -3-indolyl; 4,5,6,7-tetrahydro-2-indolyl; cyclohepta[b]-5-pyrrolyl; 2-, 3- or 4-quinolyl; 1-, 3- or 4-isoquinolyl; 1-oxo-1,2-dihydro-3-isoquinolyl; 2-quinoxalinyl; 2-benzofuranyl; 2-benzoxazolyl; benzothiazolyl; benz[e]indol-2-yl or β-carbolin-3-yl.

Partially hydrogenated or completely hydrogenated heterocyclic rings are for example dihydropyridinyl; pyrrolidinyl, for example 2-, 3- or 4-N-methylpyrrolidinyl; piperazinyl; morpholino; thiomorpholino; tetrahydrothiophenyl; benzodioxolanyl.

Halogen is fluorine, chlorine, bromine or iodine, in particular fluorine or chlorine.

Salts of compounds of the formula (I) are taken in particular to mean pharmaceutically usable or non-toxic salts.

Said salts are, for example, formed from compounds of the formula (I) which contain acid groups, for example carboxy, with alkali metals or alkaline earth metals, such as, for example, Na, K, Mg and Ca, and with physiologically tolerated organic amines, such as for example triethylamine and tris(2-hydroxyethyl)amine.

Compounds of the formula (I) which contain basic groups, for example an amino group or a guanidino group, form salts with inorganic acids, such as for example hydrochloric acid, sulfuric acid or phosphoric acid and with organic carboxylic or sulfonic acids, such as for example acetic acid, citric acid, benzoic acid, maleic acid, fumaric acid, tartaric acid and p-toluenesulfonic acid.

An embodiment of the process according to the invention thus comprises stereoselectively reductively dimerizing aldehydes of the formula VII with the aid of the vanadium(II) complex $[V_2Cl_3(THF)_6]2[Zn_2Cl_5]$ in inert solvents in the temperature range from −78° C. to boiling point to give the compounds of the formula I.

The abovementioned vanadium complex is used in situ (J. H. Freudenberger, A. W. Konradi, S. F. Pedersen, J. Am. Chem. Soc. 111, 8014 (1989)) or isolated from the reaction of $VCl_3(THF)_3$ (L. E. Manzer, Inorg. Syntheses 21, 135 (1982)) and zinc dust (F. A. Cotton, S. A. DuraJ, W. J. Roth, J. Inorg. Chem. 24, 913 (1985); R. J. Bouma, J. H. Teuben, W. R. Beukema, R. L. Bansemer, J. C. Huffman, K. G. Caulton, J. Inorg. Chem. 23, 2715 (1984); F. A. Cotton, S. A. Duraj, M. W. Extine, G. E. Lewis, W. J. Roth, C. D. Schmulback, W. J. Schwotzer, Chem. Soc. Chem. Commun., 1377 (1983)).

A preferred embodiment for preparation of the compounds of the formula I having the abovementioned preferred configuration comprises introducing $VCl_3(THF)_3$ into an apparatus flushed with a protecting gas (for example $N_2$ or argon) in inert solvents, such as cyclic or acyclic dialkyl ethers, aromatic hydrocarbons or alkyl hydrocarbons, or halogenated hydrocarbons, in particular dichloromethane, di-, tri- or tetrachloroethane, toluene or THF, at temperatures from −78° C. to boiling point, preferably from 0° C. to boiling point, and successively adding 0.5 to 1.0, preferably 0.5 to 0.7 equivalent of zinc dust and 0 to 9 equivalents of a complexing agent, such as DMF, HMPA, DMSO, 1,3-dimethylimidazolidin-2-one, DABCO, TMEDA, EDTA, nitrilotriacetic acid, triethanolamine, glyme, diglyme, triglyme, ethylene glycol, diethylene glycol, crown ethers or cryptands, preferably 2 to 7 equivalents of HMPA, and 0.2 to 1.0, preferably 0.4 to 0.6 equivalent of an aldehyde of the formula VII and stirring the mixture under an atmosphere of protecting gas (for example $N_2$ or argon) at the respective initial temperature until completion of the reaction according to TLC monitoring. For work-up the reaction temperature is adjusted to room temperature and the aqueous solution of a complexing agent, preferably 10 to 30% strength aqueous citric acid solution or tartrate solution, is added to the mixture. After phase separation the aqueous phase is extracted with the solvent used in the reaction mixture or instead with an organic water-immiscible solvent, the combined organic phases are dried, filtered and evaporated to dryness, the crude product being obtained in yields from 20% to 100% of theory. Purification is preferably carried out by crystallization or chromatography on a silica gel column or is not required because of the satisfactory purity of the crude product obtained.

The particularly preferred compounds of the formula I in the SRRS configuration are preferably obtained from the α-aminoaldehydes of the formula VII having S configuration at room temperature or elevated temperature.

Optically pure α-aminoaldehydes of the formula VII are obtained from amino acids in a simple manner disclosed by the literature, for example as illustrated in more detail below.

Commercially available or laboratory-synthesized compounds of the formula IX

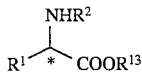  (IX)

in which $R^{13}$ is H, $(C_1-C_4)$-alkyl, $(C_6-C_{14})$-aryl or $(C_6-C_{14})$-aryl $(C_1-C_6)$-alkyl, in particular methyl, ethyl or benzyl and $R^1$ and $R^2$ are defined as above (Houben Weyl 15/1 and 2, Stuttgart, 1974; V. Teetz, R. Geiger, H. Gaul, Tetrahedron Letters 25(40), 4479 (1984); A. Pictet, T. Spengler, Chem. Ber. 44,2030 (1911); R. M. Williams, "Synthesis of Optically Active α-Aminoacids", Pergamon Press, Oxford, 1989) are reduced, analogously to methods disclosed in the literature (M. W. Drewes, "The Syntheses and Stereoselective Reactions of α-Aminoaldehydes", inaugural dissertation, Department of Chemistry of the Philipps University, Marburg/Lahn 1988; and literature cited therein; N. G. Gaylord, "Reduction with Complex Metal Hydrides", Interscience Publishers, N.Y. London, 1956; H. Schenker, Angew. Chemie 73, 81 (1961); C. F. Stanfield, J. E. Parker, P. Kanellis, J. Org. Chem. 46, 4797 and 4799 (1981); K. E. Rittle, C. F. Homnick, B. E. Evans, J. Org. Chem.47, 3016 (1982); K. Haaf, C. Rüchardt, Chem. Ber.123, 635 (1990)) for example using $NaBH_4$ (N. G. Gaylord, see above), $BH_3$·THF (K. E. Rittle, see above), or $LiAlH_4$ (K. Haaf, see above) in inert solvents, or lower alcohols or aqueous alcohol mixtures, to give the amino alcohols of the formula X,

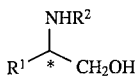  (X)

$R^1$ and $R^2$ being defined as above. The compounds of the formula X thus obtained are subsequently reacted by known processes (Houben Weyl, see above; E. Gross, J. Meinhofer, Ed., "The Peptides—Protection of Functional Groups in Peptide Synthesis", Academic Press, N.Y., 1981; T. W. Greene, "Protective Groups in Organic Synthesis", John Wiley & Sons, N.Y. Chichester Brisbane Toronto Singapore, 1980; Proceedings of European Peptide Symposium, Platja D'Aro, September 1990 (EP 0 460 446) to give the compounds of the formula XI

  (XI)

having the meanings mentioned for $R^1$–$R^3$, which are subsequently oxidized using pyridinium dichromate (C. F. Stanfield, see above), $CrO_3$·pyridine (K. E. Rittle, see above), but in particular using $(COCl)_2$ and DMSO, by the method of Swern without racemization to give the aldehydes of the formula VII

  (VII)

$R^1$, $R^2$ and $R^3$ being defined as above (K. Omura, A. K. Sharma, D. Swern, J. Org. Chem.41, 957 (1976); D. Swern, S. L. Huang, A. J. Mancuso, J. Org. Chem.43, 2480 (1978); A. J. Mancuso, D. Swern, Synthesis, 165 (1981)).

A second variant comprises reacting compounds of the formula IX, analogously to the abovementioned syntheses known from the literature, to give compounds of the formula XII

  (XII)

in which $R^1$, $R^2$, $R^3$ and $R^{13}$ are defined as above, and reacting these compounds—possibly after a preceding non-racemizing hydrolysis of an ester of the formula XII where $R^{13} \neq H$— for example according to the method of Weinreb (S. Nahm, S. M. Weinreb, Tetrahedron Letters 22, 3815 (1981)) with N,O-dimethylhydroxylamine to give compounds of the formula XIII,

  (XIII)

$R^1$, $R^2$ and $R^3$ being defined as above. The amides of the formula XIII are converted, for example according to the method of Castro (J. A. Fehrentz, B. Castro, Synthesis, 676 (1983); J. A. Fehrentz, B. Castro, Int. J. Peptide Protein Res. 26, 236 (1985)), by reduction with $LiAlH_4$ directly and without racemization into the aldehydes mentioned of the formula VII.

In a third variant carboxylic acids of the formula XII ($R^{13}$=H) are derivatized using thionyl chloride or other suitable halogenating agents to give the corresponding carbonyl halides of formula XIV

  (XIV)

$R^1$–$R^3$ corresponding to the above definitions and $R^{14}$ being Cl, Br, I or radicals of mixed carboxylic anhydrides, which are subsequently reduced using $H_2/Pd/BaSO_4$ without racemization to give the aldehydes of the formula VII (by analogy with: R. L. Johnson, J. Med. Chem. 25,605 (1982)). In principle aldehydes can also be prepared from carboxylic acids and their derivatives using other methods, for instance by reaction with simple and complex metal hydrides, metal carbonyl complexes, silanes, alkali metals or formates, or photochemically (Houben Weyl 7E3, 418ff, Stuttgart, 1983).

In contrast to the pinacol couplings described in Pedersen et al. (J. H. Freudenberger, see above; A. W. Konradi, S. F. Pedersen, J. Org. Chem. 55, 4506 (1990); P. M. Takahara, J. H. Freudenberger, A. W. Konradi, S. F. Pedersen, Tetrahedron Letters 30 (51), 7177 (1989); A. S. Raw, S. F. Pedersen, J. Org. Chem. 56,830 (1991)), in the present process simultaneous control is exercised over four stereo centers. With the use of optically active starting materials, optically active coupling products are obtained in high yield. A further advantage of the process described here is the higher selectivity of the reducing agent for the activated aldehyde function, which leads to greater compatibility with other functional groups. As J. E. McMurry (Chem. Rev. 89, 1513 (1989), in particular Table 2, p. 1515) describes, the McMurry reagent is only semi-compatible with functional groups such as, for example, amide, carboxylic acid, ester and ketone and incompatible with functional groups such as nitro, oxime, sulfoxide, epoxide and 1,2-diol. On the other hand, the vanadium complex is, for example, completely compatible with the amide function and even non-activated aldehyde functions do not react at an appreciable rate (J. H. Freudenberger, see above, in particular p. 8016).

Abbreviations used:

| Cha | cyclohexylalanine |
|---|---|
| Chg | cyclohexylglycine |
| DABCO | 1,4-diazabicyclo[2.2.2]octane |
| DMF | dimethylformamide |
| DMSO | dimethylsulfoxide |
| EDTA | ethylenediaminetetraacetic acid |
| HMPA | hexamethylphosphoric acid triamide |
| MTB | methyl tert-butyl |
| Nal | 1- and 2-naphthylalanine |
| Npg | neopentylglycine |
| Tbg | tert-butylglycine |
| THF | tetrahydrofuran |
| Thia | 2-thienylalanine |
| TMEDA | N,N,N',N'-tetramethylethylenediamine |

By means of the following examples the process according to the invention is further illustrated and specific embodiments are described. These examples and embodiments limit the invention neither with respect to the structural variety of the α-aminoaldehydes VII diastereoselectively reductively dimerized in this manner, nor with respect to the process conditions (reagent preparation, physical parameters of the reductive dimerization, solvents, reaction time, work-up, purification and analysis of the reaction products).

EXAMPLE 1

N-(tert-butoxycarbonylamino)-(S)-phenylalanine-N-methoxy-N-methylamide 88.1 g (332 mmol) of (S)-phenylalanine are dissolved in 1.2 l of dichloromethane and 268 ml (2.1 mol) of ethylmorpholine and 43.7 g (445 mmol) of N,O-dimethylhydroxylamine hydrochloride are added under a nitrogen atmosphere at a constant internal temperature of 20° C. (cooling using an ice bath). The reaction mixture is cooled to −10° C., and a solution of 252 ml of propanephosphonic anhydride in 250 ml of ethyl acetate is added dropwise. By means of continued stirring (1 h at 0° C., subsequently 2 h at room temperature), complete conversion of the reactants is achieved. The mixture is washed with 1 l of 3 N HCl, 800 ml of saturated, aqueous NaHCO$_3$ solution and 800 ml of saturated aqueous NaCl solution and the organic phase is dried over Na$_2$SO$_4$. After evaporation of the solvent, there remain 100 g of a colorless oil, which can be used, without further purification, in the reduction to give the corresponding aminoaldehyde.

EXAMPLE 2

N-(tert-butoxycarbonyl)-(S)-phenylalaninal 4.36 g of lithiumaluminum hydride are taken in 875 ml of dry diethyl ether under a nitrogen atmosphere at 0° C. and a solution of 26.9 g of N-(tert-butoxycarbonylamino)-(S)-phenylalanine-N-methoxy-N-methylamide in 73 ml of diethyl ether is added with stirring. The mixture is stirred for 30 min at 0° C., and then 450 ml of 5% strength cold aqueous KHSO$_4$ solution are added. The phases are separated, the organic phase is successively washed with 300 ml of 0.5 N HCl, 600 ml of saturated aqueous NaHCO$_3$ solution and 600 ml of saturated aqueous NaCl solution and is finally dried over Na$_2$SO$_4$. After evaporation of the solvent there remain 20.9 g (96.3%) of white crystals, which may be used without further purification for the reductive coupling.

EXAMPLE 3

N-(tert-butoxycarbonylvalinyl)amino)-(S)-phenylalaninal 2.1 ml (25 mmol) of oxalyl chloride are dissolved in 125 ml of dry dichloromethane under an inert gas atmosphere. At −70° C., 2.4 ml (33.4 mmol) of DMSO are added dropwise with stirring and, after a waiting time of 15 min, a solution of 5.85 g (16.7 mmol) of N-(tert-butoxycarbonyl)-(S)-valyl-(S)-phenylalaninol in a mixture of 4 ml of DMSO and 30 ml of dichloromethane is slowly added. The reaction mixture is stirred for 30 min at −70° C. and then 9.4 ml (66.8 mmol) of triethylamine are added dropwise, the temperature rising to −60° C. After a further 15 min at −60° C., the mixture is hydrolyzed using 200 ml of 15% strength aqueous citric acid and the phases are separated. The organic phase is successively washed with 200 ml each time of saturated aqueous bicarbonate solution, water, and finally saturated aqueous sodium chloride solution, and dried over sodium sulphate. After evaporation of the solvent there remain 4.4 g of white crystals, which can be used, without further purification steps, for the dimerization.

General experimental procedure for the reductive coupling:

2.3 equivalents of trichlorotris(tetrahydrofuran) vanadium(III) are taken in 15 ml of dry solvent under an inert gas atmosphere and are reduced by addition of 1.3 equivalents of zinc dust at room temperature. After stirring for 30 minutes, 5.6 equivalents of complexing agent are added to the reaction mixture and the mixture is brought to the reaction temperature. At a stable temperature, 1 equivalent of the corresponding aldehyde in 3 ml of dry solvent is added, and the conversion of the reactants is monitored by means of TLC. After completion of the reaction, shaking the mixture at room temperature with 1.) sodium tartrate solution and 2.) cold citric acid (in each case 20 ml of a 10% strength aqueous solution), drying the organic phase over Na$_2$SO$_4$ and removing the solvent by suction produces a colorless, oily residue, which is purified by means of chromatography on silica gel and/or by means of crystallization.

EXAMPLE 4

N,N'-bis-(tert-butoxycarbonyl)-2S,5S-diamino-1,6-diphenylhexane-3R,4R-diol

Starting from 5 g of N-(tert-butoxycarbonyl)-(S)phenylalaninal, white crystals of the title compound are obtained analogously to the general procedure (solvent: $CH_2Cl_2$; complexing agent: HMPA; reaction temperature: room temperature).

Yield: 0.8 g of a mixture of the 2S,3S,4S,5S-/2S,3R,4S,5S-isomers (melting point: 163° C.) 3.3 g of pure 2S,3R,4R,5S-isomer (melting point: 200° C.)

Rf values: ethyl acetate/cyclohexane=60:40 0.6 (mixture of 2S, 3S, 4S, 5S-/2S, 3R, 4S, 5S isomers) 0.3 (pure 2S, 3R, 4R, 5S-isomer)

MS (FAB): 501 (M+H$^+$), 401,345,301; 2S,3S,4S,5S/2S, 3R,4S,5S 501 (M+H$^+$), 401, 345, 301; 2S,3R,4R,5S $^1$H-NMR (270 MHz, DMSO-D$_6$) 2S,3R,4R,5S isomer: 7.1–7.3 (m, 10H, H$_{arom.}$); 6.2 (d, 2H, N-H); 4.4 (m, 2H, OH); 4.1 (m, 2H, H$^3$+H$^4$); 3.2 (m, 2H, H$^2$+H$^5$); 2.5–2.8 2H, CH$_2$); 1.3 (s, 18H, tert-butyl)

EXAMPLE 5

N,N'-bis-(tert-butoxycarbonyl)-2S,5S-diamino-1,6-dicyclohexylhexane-3R,4R-diol Starting from 3 g of N-(tert-butoxycarbonyl)-(S)-cyclohexylalaninal, 2 g of white crystals of the title compound are obtained analogously to the general procedure (solvent: $CH_2Cl_2$; complexing agent: HMPA; reaction temperature: room temperature).

MS (FAB): 506 (M+H$^+$), 406, 306

EXAMPLE 6

(2S,3R,4R,5S)-2,5-(N,N'-(tert-butoxycarbonyl-(S)-valinyl) amino)-3,4-dihydroxy-1,6-diphenylhexane Starting from 4.4 g of N-(tert-butoxycarbonyl)-(S)-valinyl-phenylalaninal, 3.2 g of white crystals of the title compound are obtained analogously to the general procedure (solvent: $CH_2Cl_2$; complexing agent: HMPA; reaction temperature: room temperature).

Melting point: 201° C.

MS (FAB) 705 (M+H$^+$), 505, 357, 257

Experimental procedure for the reductive coupling with in situ production of the coupling reagent 2.01 mmol of vanadium trichloride are boiled under reflux for 5 h under an inert gas atmosphere in 4.5 ml of absolute THF. After cooling to room temperature, 1.3 mmol of zinc dust are added, the mixture is stirred for 30 min, 5.6 mmol of complexing agent are added and the mixture is heated again to reflux. After the reflux temperature is attained, 2 mmol of the corresponding aldehyde in 1 ml of dry THF are rapidly added. The complete conversion of the reactants is monitored by means of TLC. The work-up and purification are carried out as described in the general experimental procedure (cf. page 31).

EXAMPLE 7

1,2-bis[N-(tert-butoxycarbonyl)-(S)-1,2,3,4-tetrahydroisoquinoline-3-yl]ethane-1(R),2(R)-diol Starting from 0.8 g of N-(tert-butoxycarbonyl)-1,2,3,4-tetrahydroisoquinoline-3 (S)-carbaldehyde, 0.28 g of colorless crystals of the title compound are obtained analogously to the experimental procedure with in situ production of the coupling reagent (complexing agent: 1,3-dimethylimidazolidin-2-one).

Melting point: 203° C.

MS (FAB) 525 (M+H$^+$), 425, 325

EXAMPLE 8

(2S,3R,4R,5S)-2,5-(N,N'-(benzyloxycarbonyl-(S)-valinyl) amino)-3,4-dihydroxy-1,6-diphenylhexane Starting from 764 mg of N-benzyloxycarbonyl-(S)-valinylphenylalaninal, 420 mg of white crystals of the title compound are obtained analogously to the experimental procedure with in situ production of the coupling reagent (complexing agent: 1,3-dimethylimidazolidin-2-one)

Melting point: 201° C.

MS (FAB): 767 (M+H$^+$), 497

EXAMPLE 9

1,2-bis[N[{2(S)-(1,1-dimethylethylsulfonylmethyl) 3-(1-naphthyl)-propionyl}-(S)-valyl]-(S) 1,2,3,4-tetrahydroisoquinoline-3-yl]ethane-1(R), 2(R)-diol Starting from 1.5 g of N[{(S)-2-(1,1-dimethyl-ethylsulfonylmethyl)-3-(1-naphthyl)propionyl}-(S)-valyl ](S)-1,2,3,4-tetrahydroisoquinoline-3-carbaldehyde, 0.3 g of yellowish crystals of the title compound are obtained analogously to the experimental procedure with in situ production of the coupling reagent (complexing agent: 1,3-dimmethylimidazolidin-2-one).

Melting point: 152° C. (decomposition)

MS (FAB): 1162 (M+Li$^+$), 1156 (M+H$^+$), 741, 388

EXAMPLE 10

N,N'-bis-(tert-butoxycarbonyl)-2S,5S-diamino-1,6-diphenylhexane-3R,4R-diol

Starting from 5 g of N-(tert-butoxycarbonyl)-(S)-phenylalaninal, 3.4 g of white crystals of the title compound are obtained analogously to the experimental procedure with in situ production of the coupling reagent (complexing agent: 1,3-dimethylimidazolidin-2-one).

Melting point: 200° C.

MS (FAB): 501 (M+H$^+$), 401, 345, 301

EXAMPLE 11

N,N'-bis[{(S)-2-(1,1-dimethylethylsulfonylmethyl)-3-(1-naphthyl)-propionyl}-(S)-valyl]-2 (S),5(S)-diamino-1,6-diphenylhexane-3(R),4(R)-diol Starting from 30.0 g of [{(S)-2-(1,1-dimethyl-ethylsulfonylmethyl)-3-(1-naphthyl)propionyl}-(S)-valyl ]-(S)-phenylalaninal, 16.5 g of colorless crystals of the title compound are obtained analogously to the experimental procedure with in situ production of the coupling reagent (complexing agent: 1,3-dimethylimidazolidin-2-one).

Melting point: 187° C.

MS (FAB): 1153 (M+Na⁺), 1131 (M+H⁺), 716, 416

EXAMPLE 12

(2S,3R,4R,5S)-2,5-Bis-[N-(benzyloxycarbonyl) amino]-1,6-diphenyl-3,4-hexanediol 50 ml of absol. THF is added to 1.73 g of vanadium trichloride and the mixture is refluxed 4 hr under nitrogen. It is cooled to room temperature and 0.39 g of zinc powder is added. A solution of 2.83 g (S)-[N-(benzyloxycarbonyl)]-phenylalaninal in 10 ml of absol. THF is added at room temperature and the mixture is refluxed I hr. The colour changes to dark-brown. Tlc (silicagel; ethylacetate/n-heptane 1:1 ) indicates quantitative transformation of the educt ($R_f$=0.36) to the product ($R_f$= 0.11 ). The mixture is cooled to room temperature, 50 ml of 2 N hydrochloric acid is added, and the mixture is stirred for 30 min.

50 ml of dichloromethane is added to induce separation of the phases. The organic layer is separated and washed with 15 ml of saturated sodium bicarbonate solution and with 15 ml of brine. The organic phase is dried with magnesium sulfate and the solvent is evaporated in vacuo. The residue (3.7 g) is digerated with 30 ml of diisopropylether and suction—filtered. Yield: 2.58 g (91%); m.p. 207°–209° C.; >97% (S,R,R,S)-isomer by HPLC.

An analytically pure sample is obtained by recrystallization from THF/hexane: m.p. 218°–219° C.;

$[\alpha]^{20}_D$=−15.2° (c=2, THF); FAB-MS (NBA): 569 (M+H⁺ ), 525, 307, 289.

EXAMPLE 13 (compare Examples 4, 14 and 15)

(2S,3R,4R,5S)-2,5-Bis-[N-(tert-butoxycarbonyl) amino]-1,6-diphen yl-3,4-hexanediol The suspension of 6.2 g vanadium trichloride in 165 ml absol. THF is degassed with argon and then refluxed 5 hr under argon. After cooling to room temperature 1.53 g of zinc powder is added. The mixture is stirred for 0.5 hr and 14.6 ml of 1,3-dimethylimidazolidin-2-one is added by syringe. The mixture is heated to reflux under argon and the solution of 4.6 g N-(tert-butoxycarbonyl)-(S)-phenylalaninal in 20 ml of absol. THF is added at once. The mixture is refluxed 2 hr under argon. Tlc (acetone/dichloromethane 1:3) indicates incomplete reaction after 1 hr and quantitative reaction after 2 hr. The mixture is allowed to stand at room temperature overnight. 500 ml of ethylacetate is added and the solution is washed with 2×250 ml 15% citric acid solution and with 2×250 ml of water. The organic phase is dried over magnesium sulfate and the solvents are evaporated in vacuo to obtain 3.97 (86%) of a pale-greenish solid, 40 % (S,R,R,S)-isomer by HPLC.

EXAMPLE 14 (compare Examples 4, 13 and 15)

(2S,3R,4R,5S)-2,5-Bis-[N-(tert-butoxycarbonyl) amino]-1,6-diphenyl-3,4-hexanediol Attempted preparation by coupling in the absence of a complexing agent at 22° C.

The suspension of 3.1 g vanadium trichloride in 85 ml absol. THF is degassed with argon and then refluxed 5 hr under argon. After cooling to room temperature 760 mg of zinc powder is added. The mixture is stirred for 0.5 hr. A solution of 2.8 g N-(tert-butoxycarbonyl)-(S)-phenylalaninal in 30 ml of absol. THF is added at 22° C. and the mixture is stirred 3 hr at ambient temperature. Tlc indicates that no coupling reaction took place.

7.3 ml of 1,3-dimethylimidazolin-2-one is added and stirring continued at 22° C. Tlc after 3 hr indicates incomplete, after 16 hr quantitative transformation of the educt to the coupling product.

EXAMPLE 15 (compare Examples 4, 13 and 14 )

(2S,3R,4R,5S)-2,5-Bis[N-(tert-butoxycarbonyl) amino]-1,6-diphenyl-3,4-hexanediol prepared by coupling in the presence of a complexing agent at 22° C.

In a reaction conducted exactly as described in example 14, but with addition of 7.3 ml of 1,3-dimethylimidazolin-2-one immediately before the addition of the aldehyde solution, educt aldehyde is transformed at 22° C. to the title product. The transformation is largely complete after 4 hr and quantitative after 16 hr.

We claim:

1. A process for the preparation of a compound of the formula I

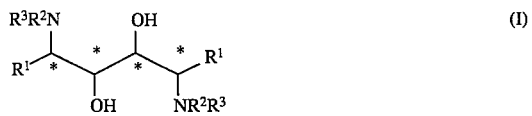

in which $R^1$ is a side chain radical of a natural or synthetic α-amino acid;

$R^2$ and $R^3$ are identical or different and are each selected from
a) hydrogen and
b) a radical of the formula

where E, F and G independently of each other are a natural or synthetic amino acid, azaamino acid or imino acid;

n, o, and p independently of each other are 0 or 1;

D is $R^4$ or a radical of the formula III, IV or V

in which $R^4$ is
b₁) hydrogen,
carboxyl, $(C_1-C_{18})$-alkyl, which is optionally monounsaturated or diunsaturated and which is unsubstituted or substituted by up to 3 identical or different radicals selected from the group comprising mercapto,
hydroxyl,
$(C_1-C_7)$-alkoxy,
carbamoyl,
$(C_1-C_8)$-alkanoyloxy,
carboxyl,
$(C_1-C_7)$-alkoxycarbonyl,
F, Cl, Br, I,
amino,
amidino, which can be unsubstituted or substituted by one, two or three $(C_1-C_8)$-alkyl radicals,
guanidino, which can be unsubstituted or substituted by one or two benzyloxycarbonyl radicals or by one, two, three or four $(C_1-C_8)$-alkyl radicals,
$(C_1-C_7)$-alkylamino,
di-$(C_1-C_7)$-alkylamino,
$(C_1-C_6)$-alkoxycarbonylamino,
$(C_7-C_{15})$-aralkoxycarbonyl,
$(C_7-C_{15})$-aralkoxycarbonylamino,
phenyl-$(C_1-C_4)$-alkoxy,
9-fluorenylmethoxycarbonylamino,
$(C_1-C_6)$-alkylsulfonyl,
$(C_1-C_6)$-alkylsulfinyl,
$(C_1-C_6)$-alkylthio,
hydroxamino,
hydroximino,
sulfamoyl,
sulfo,
carboxamido,
formyl,
hydrazono,
imino,
a $CONR^9R^{10}$ radical,
by up to six hydroxyl groups and
by up to five $(C_1-C_6)$-alkanoyloxy groups;

mono-, bi- or tricyclic $(C_3-C_{15})$-cycloalkyl,
$(C_3-C_{18})$-cycloalkyl-$(C_1-C_6)$-alkyl, the cycloalkyl moiety being unsubstituted or substituted by one or two identical or different radicals selected from the group consisting of F, Cl, Br, I,
carboxyl,
carbamoyl,
carboxymethoxy,
hydroxyl,
$(C_1-C_7)$-alkoxy,
$(C_1-C_7)$-alkyl
$(C_1-C_7)$-alkyloxycarbonyl,
amino,
$(C_1-C_6)$-alkylamino-$(C_1-C_6)$-alkyl,
di-$(C_1-C_6)$-alkylamino-$(C_1-C_6)$-alkyl,
amidino,
hydroxamino,
hydroximino,
hydrazono,
imino,
guanidino,
$(C_1-C_6)$-alkoxysulfonyl,
$(C_1-C_6)$-alkoxysulfinyl,
$(C_1-C_6)$-alkoxycarbonylamino,
$(C_6-C_{12})$-aryl-$(C_1-C_4)$-alkoxycarbonylamino,
$(C_1-C_7)$-alkylamino,
di-$(C_1-C_7)$-alkylamino and
trifluoromethyl;
$(C_6-C_{14})$-aryl,
$(C_6-C_{14})$-aryl-$(C_1-C_6)$-alkyl,
$(C_6-C_{14})$-aryloxy-$(C_1-C_6)$-alkyl or
$(C_6-C_{14})$-aryl-$(C_3-C_8)$-cycloalkyl, in which the aryl moiety in each case is unsubstituted or substituted by one, two or three identical or different radicals selected from the group consisting of F, Cl, Br, I,
hydroxyl,
mono-, di- or trihydroxy-$(C_1-C_4)$-alkyl,
trifluoromethyl,
formyl,
carboxamido,
mono- or di-$(C_1-C_4)$-alkylaminocarbonyl,
nitro,
$(C_1-C_7)$-alkoxy,
$(C_1-C_7)$-alkyl,
$(C_1-C_7)$-alkoxycarbonyl,
amino,
$(C_1-C_7)$-alkylamino,
di-$(C_1-C_7)$-alkylamino,
carboxyl,
carboxymethoxy,
amino-$(C_1-C_7)$-alkyl,
$(C_1-C_7)$-alkylamino-$(C_1-C_7)$-alkyl,
di-$(C_1-C_7)$-alkylamino-$(C_1-C_7)$-alkyl,
$(C_1-C_7)$-alkoxycarbonylmethoxy,
carbamoyl,
sulfamoyl,
$(C_1-C_7)$-alkoxysulfonyl,
$(C_1-C_8)$-alkylsulfonyl,
sulfo-$(C_1-C_8)$-alkyl,
guanidino-$(C_1-C_8)$-alkyl and
$(C_1-C_6)$-alkoxycarbonylamino;

het,
het-$(C_1-C_6)$-alkyl,
het-$(C_3-C_8)$-cycloalkyl,
het-$(C_3-C_8)$-cycloalkyl-$(C_1-C_4)$-alkyl,
het-$(C_3-C_8)$-cycloalkoxy-$(C_1-C_4)$-alkyl,
het-thio-$(C_1-C_6)$-alkyl,
het-thio-$(C_3-C_8)$-cycloalkyl, and
het-thio-$(C_3-C_8)$-cycloalkyl-$(C_1-C_4)$-alkyl, het being in each case the radical of a 5- to 7-membered monocyclic or 8- to 10-membered bicyclic ring system, which may be fused to a benzene ring, be aromatic, or partially or completely hydrogenated, which can contain as hetero elements one, two, three or four different radicals selected from the group consisting of N, O, S, NO, SO, and $SO_2$, which can be substituted by 1 to 6 hydroxyl groups and which is optionally defined as for $(C_6-C_{14})$-aryl under $b_1$) and/or is mono-, di- or trisubstituted by oxo, or is an $NR^9R^{10}$ radical: or $b_2$) a radical of the formula VI $$R^{4a}\text{-W} \qquad (VI)$$

in which $R^{4a}$ is defined as for $R^4$ under $b_1$) and W is —CO—, —CS—, O—CO—, —$SO_2$—, —SO—, —S—, —$NHSO_2$—, —NHCO—, —CH(OH)—, —N(OH)— or —CO—V—, V being a peptide having a total of 1 to 10 amino acids, imino acids and/or azaamino acids; or in which $R^4$ together with $R^6$ and the atoms bearing these form mono- or bicyclic, saturated or partially unsaturated ring systems having 5–12 ring members, which can also contain, apart from carbon, 1 sulfur atom which can optionally be oxidized to the sulfoxide or sulfone; or b₃) a glycosyl radical which is derived from naturally occurring aldotetroses, aldopentoses, aldohexoses, ketopentoses, ketohexoses, deoxyaldoses, aminoaldoses, oligosaccharides or their stereoisomers; or b₄) an amino-protecting group;

$R^5$ is hydrogen or $(C_1-C_8)$-alkyl, or together with $R^6$ and the atoms bearing this radical forms mono- or bicyclic, saturated or partially unsaturated ring systems having 5–12 ring members;

$R^6$ is defined as for $R^4$ under $b_1$);

is hydroxyl or $(C_1-C_4)$-alkanoyloxy; or together with $R^7$ and the atoms bearing this radical forms cyclic, saturated or partially unsaturated ring systems having 3 to 12 ring members; or together with $R^8$ and the atoms bearing this forms a mono- or bicyclic, saturated or partially unsaturated ring system having 5–12 ring members, which can also contain, apart from carbon, 1 sulfur atom which can optionally be oxidized to the sulfoxide or sulfone; or can contain 1 nitrogen atom, where the ring system can be unsubstituted or substituted by amino;

$R^7$ is hydrogen or $(C_1-C_6)$-alkyl;

$R^8$ is hydrogen, hydroxyl, $(C_1-C_4)$-alkanoyloxy or $(C_1-C_8)$-alkyl;

$R^9$ and $R^{10}$ are each hydrogen, $(C_1-C_8)$-alkyl, which can be substituted by
 amino,
 $(C_1-C_4)$-alkylamino,
 di-$(C_1-C_4)$-alkylamino,
 mercapto,
 carboxyl,
 hydroxyl or
 $(C_1-C_4)$-alkoxy, $(C_3-C_7)$-cycloalkyl, $(C_1-C_4)$-alkoxycarbonyl, $(C_6-C_{14})$-aryl, $(C_6-C_{14})$-aryl-$(C_1-C_4)$-alkoxycarbonyl, which can be substituted in the aryl moiety as described for $R^4$, het or het-$(C_1-C_4)$-alkyl, her being defined as described for $R^4$, or $R^9$ and $R^{10}$ together with the nitrogen atom bearing them forming monocyclic or bicyclic, saturated, partially unsaturated or aromatic ring systems which contain as ring members, in addition to carbon, 1 or 2 further nitrogen atoms, 1 sulfur atom or 1 oxygen atom and can be substituted by $(C_1-C_4)$-alkyl, where in the preceding compounds of the formula I one or more amide groups (—CONH—) of the main chain can be replaced by —CH₂—NR¹¹—, —CH₂S—, —CH₂O—, —OCH₂—, —CH₂CH₂—, —CH=CH— (cis or trans), —COCH₂—, —CH(OH)CH₂—, —CH₂SO—, —CH₂SO₂—, —COO—, —P(O)(OR¹²)CH₂—, —P(O)(OR¹²)NH—, or by an amide group having reversed polarity (—NHCO—);

in which $R^{11}$ and $R^{12}$ independently of each other are hydrogen or $(C_1-C_4)$-alkyl;

and their enantiomers and physiologically tolerated salts, which comprises treating a homochiral α-aminoaldehyde of the formula VII

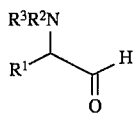

in which $R^1$, $R^2$ and $R^3$ are defined as above, with $[V_2Cl_3(THF)_6]_2[Zn_2Cl_6]$ or with a vanadium complex obtainable in situ from $VCl_3$, THF and zinc dust, a simultaneous control over all four chiral centers being present.

2. The process for the preparation of a compound of the formula I as claimed in claim 1, wherein $R^1$ is a side chain radical of the α-amino acids Gly, Ala, Val, Leu, Ile, Ser, Thr, Cys, Met, Pro, Lys, Arg, His, Asp, Asn, Glu, Gln, Phe, Tyr, Trp or Cha;

$R^2$ and $R^3$ are identical or different and are each a) hydrogen or b) a radical of the formula II
 in which o and p=0,
 n=0 or 1 and
 E is one of the abovementioned α-amino acids,
 D is $R^4$ or a radical of the formula III or IV, in which $R^4$ is b₁) hydrogen $(C_1-C_9)$-alkyl, which is optionally monounsaturated or diunsaturated and which is unsubstituted or substituted by up to 3 identical or different radicals selected from the group consisting of
 hydroxyl,
 $(C_1-C_7)$-alkoxy,
 carbamoyl,
 $(C_1-C_8)$-alkanoyloxy,
 $(C_1-C_7)$-alkoxycarbonyl,
 F, Cl,
 amino,
 $(C_1-C_7)$-alkylamino,
 di-$(C_1-C_7)$-alkylamino,
 $(C_1-C_6)$-alkoxycarbonylamino,
 $(C_7-C_{15})$-aralkoxycarbonyl,
 $(C_7-C_{15})$-aralkoxycarbonylamino,
 phenyl-$(C_1-C_4)$-alkoxy,
 9-fluorenylmethoxycarbonylamino,
 $(C_1-C_6)$-alkylsulfonyl,
 $(C_1-C_6)$-alkylsulfinyl, and
 $(C_1-C_6)$-alkylthio, $(C_6-C_{14})$-aryl, $(C_6-C_{14})$-aryl-$(C_1-C_6)$-alkyl or $(C_6-C_{14})$-aryloxy-$(C_1-C_6)$-alkyl, in which the aryl moiety may in each case be unsubstituted or substituted by one, two or three identical or different radicals selected from the group consisting of the abovementioned substituents of $(C_1-C_9)$-alkyl, b₂) a radical of the formula VI, in which $R^{4a}$ is defined as for $R^4$ under $b_1$) and W is —CO—, O—CO—, —SO₂—, —SO—, —S—, —NHCO—, or —CH(OH)—; or b₄) an amino-protecting group Fmoc, Z or Boc, $R^5$ and $R^7$ are each hydrogen, $R^6$ is defined as for $R^4$, and $R^8$ is hydrogen, hydroxyl,
(C$_1$–C$_4$)-alkanoyloxy or
(C$_1$–C$_8$)-alkyl.

3. The process for the preparation of a compound of the formula I as claimed in claim 1, wherein one of the radicals R$^2$ and R$^3$ is hydrogen.

4. The process for the preparation of a compound of the formula I as claimed in claim 1, wherein the compound of the formula I has the SRRS-configuration or the RSSR-configuration.

5. The process for the preparation of a compound of the formula I as claimed in claim 1, wherein R$^1$ is a side chain radical of the α-amino acids Ala, Val, Leu, Ile, Pro, Phe, Cha or Tyr, R$^2$ and R$^3$ are identical or different and are each a) hydrogen b) a radical of the formula II, in which
o and p=0,
n is 0 or 1 and
E is Ala, Val, Leu, Ile, Pro, Phe, Cha or Tyr;
D is R$^4$ or a radical of the formula IV where R$^4$ is b$_1$) hydrogen,
(C$_1$–C$_4$)-alkyl,
phenyl or naphthyl
phenylmethyl or naphthylmethyl;

b$_2$) a radical of the formula VI, in which R$^{4a}$ is defined as for R$^4$ under b$_1$) and W is —CO—, —O—CO—, —SO$_2$—, —SO—, —S—, —NHCO—, or —CH(OH)—, or b$_4$) an amino-protecting group Fmoc, Z or Boc, R$^5$, R$^7$ and R$^8$ are each hydrogen, and R$^6$ is defined as for R$^4$ under b$_1$).

6. The process for the preparation of a compound of the formula I as claimed in claim 1, wherein VCl$_3$(THF)$_3$ is introduced into an apparatus flushed with a protecting gas in inert solvents at temperatures from −78° C. to boiling point and 0.5 to 1.0 equivalent of zinc dust and 0 to 9 equivalents of a complexing agent and 0.2 to 1.0 equivalent of an aldehyde of the formula VII are successively added and the mixture is stirred under an atmosphere of protecting gas at the respective initial temperature until completion of the reaction.

7. A process for the preparation of a compound of the formula I as claimed in claim 1, wherein in b$_3$), the glycosyl radical is a glucofuranosyl or glucopyranosyl radical.

* * * * *

UNITED STATES PATENT AND TRADEMARK OFFICE
CERTIFICATE OF CORRECTION

PATENT NO. : 5,519,113
DATED : May 21, 1996
INVENTOR(S) : Joachim-Heiner JENDRALLA et al.

It is certified that error appears in the above-indentified patent and that said Letters Patent is hereby corrected as shown below:

On the title page, item [57]
In the Abstract, Title page, line 6, before "are" delete --,--.

Claim 1, column 23, line 40, "$(C_3-C_{15})$" should read --$(C_3-C_{18})$--.

Claim 1, column 24, line 55, ":" should read --;--.

Claim 1, column 24, line 65, "$R^6$" should read --$R^8$--.

Claim 5, column 27, line 17, after "a) hydrogen" insert --or--.

Claim 5, column 28, line 2, after ";" insert --or--.

Claim 5, column 28, line 6, "," should read --;--.

Signed and Sealed this

Nineteenth Day of November, 1996

Attest:

BRUCE LEHMAN

*Attesting Officer*     *Commissioner of Patents and Trademarks*